US009505686B2

(12) United States Patent
Daudin et al.

(10) Patent No.: US 9,505,686 B2
(45) Date of Patent: Nov. 29, 2016

(54) PROCESS FOR THE SELECTIVE HYDROGENATION OF A GASOLINE

(71) Applicant: IFP Energies nouvelles, Rueil-Malmaison (FR)

(72) Inventors: Antoine Daudin, Corbas (FR); Elodie Devers, Lyons (FR); Julien Gornay, Grigny (FR); Philibert Leflaive, Le Domaine de Chanteclair (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 800 days.

(21) Appl. No.: 13/851,258

(22) Filed: Mar. 27, 2013

(65) Prior Publication Data

US 2013/0261357 A1 Oct. 3, 2013

(30) Foreign Application Priority Data

Mar. 29, 2012 (FR) ...................... 12 00952

(51) Int. Cl.
| | |
|---|---|
| *C07C 7/163* | (2006.01) |
| *C07C 5/13* | (2006.01) |
| *C10G 45/04* | (2006.01) |
| *C10G 45/06* | (2006.01) |
| *C10G 45/08* | (2006.01) |
| *C10G 65/04* | (2006.01) |
| *C10G 65/06* | (2006.01) |
| *C10G 29/20* | (2006.01) |
| *C10G 45/38* | (2006.01) |
| *C10G 45/60* | (2006.01) |
| *B01J 37/20* | (2006.01) |
| *B01J 23/28* | (2006.01) |
| *B01J 23/30* | (2006.01) |
| *B01J 23/745* | (2006.01) |
| *B01J 23/75* | (2006.01) |
| *B01J 23/755* | (2006.01) |
| *B01J 23/883* | (2006.01) |
| *B01J 35/10* | (2006.01) |
| *B01J 37/02* | (2006.01) |

(52) U.S. Cl.
CPC ................ *C07C 7/163* (2013.01); *B01J 23/28* (2013.01); *B01J 23/30* (2013.01); *B01J 23/745* (2013.01); *B01J 23/75* (2013.01); *B01J 23/755* (2013.01); *B01J 23/883* (2013.01); *B01J 35/1019* (2013.01); *B01J 35/1038* (2013.01); *B01J 37/0201* (2013.01); *B01J 37/20* (2013.01); *C07C 5/13* (2013.01); *C10G 29/205* (2013.01); *C10G 45/04* (2013.01); *C10G 45/06* (2013.01); *C10G 45/08* (2013.01); *C10G 45/38* (2013.01); *C10G 45/60* (2013.01); *C10G 65/043* (2013.01); *C10G 65/06* (2013.01); *C10G 2300/104* (2013.01); *C10G 2300/1088* (2013.01); *C10G 2300/202* (2013.01); *C10G 2400/02* (2013.01)

(58) Field of Classification Search
CPC .................................. C07C 7/163; C07C 5/13
USPC .................................................... 585/253, 277
See application file for complete search history.

(56) References Cited

U.S. PATENT DOCUMENTS

| | | | |
|---|---|---|---|
| 5,137,859 A | 8/1992 | Fujikawa et al. | |
| 5,597,476 A | 1/1997 | Hearn et al. | |
| 6,013,598 A | 1/2000 | Lapinski et al. | |
| 6,126,814 A | 10/2000 | Lapinski et al. | |
| 6,896,795 B2 * | 5/2005 | Didillon ................. | B01J 23/755 208/189 |

FOREIGN PATENT DOCUMENTS

| | | | |
|---|---|---|---|
| EP | 0 451 640 | 10/1991 | |
| FR | EP 2161076 A1 * | 3/2010 | ............. B01J 23/85 |

OTHER PUBLICATIONS

Machine-translated English document of EP 2161076 A1.*

* cited by examiner

*Primary Examiner* — In Suk Bullock
*Assistant Examiner* — Youngsul Jeong
(74) *Attorney, Agent, or Firm* — Millen White Zelano and Branigan, PC; Csaba Henter; Anthony Zelano

(57) ABSTRACT

The present application relates to a process for the selective hydrogenation of a gasoline which contains polyunsaturated compounds and sulphurous light compounds, the process allowing conjointly the hydrogenation of polyunsaturated compounds into mono-unsaturated compounds, increasing weight of the sulphurous light compounds by reaction with the unsaturated compounds, and maximization of the isomerization of the monounsaturated compounds comprising an external C=C double bond into their internal C=C double bond isomer, said process implementing a catalyst containing at least one group VIb metal and at least one group VIII metal deposited on a porous support.

20 Claims, No Drawings

PROCESS FOR THE SELECTIVE HYDROGENATION OF A GASOLINE

The present invention relates to a process for selective hydrogenation of a gasoline and a desulphuration process implementing this selective hydrogenation process.

PRIOR ART

The production of gasolines which comply with the new environmental standards requires that their sulphur content be greatly reduced to values generally not exceeding 50 ppm, and preferably to below 10 ppm.

Conversion gasolines, and more particularly those produced by catalytic cracking, which can represent 30 to 50% of the gasoline pool, are furthermore known to exhibit high contents of olefins and sulphur.

For this reason, nearly 90% of the sulphur present in gasolines is attributable to the gasolines derived from catalytic cracking processes, which will be referred to hereinafter as FCC (Fluid Catalytic Cracking). The FCC gasolines thus constitute the preferred feed of the process of the present invention.

Of the possible pathways for the production of low-sulphur fuels, the one most widely used consists of specifically treating the sulphur-rich base gasolines by hydrodesulphuration in the presence of hydrogen. Conventional processes desulphur gasolines non-selectively by hydrogenating a large proportion of the mono-olefins, causing a large loss of octane index and a high consumption of hydrogen. The most recent processes, such as the Prime G+ process (commercial name), allow desulphuration of the olefin-rich cracking gasolines while limiting the hydrogenation of mono-olefins and consequently the loss of octane and high hydrogen consumption resulting therefrom. Such procedures are described, for example, in patent applications EP 1077247 and EP 1174485.

As described in patent application EP 1077247, the hydrotreatment step is advantageously preceded by a step of selective hydrogenation of the feed to be treated. This first hydrogenation step consists essentially of selectively hydrogenating the diolefins, while conjointly transforming the sulphurous saturated light compounds by weighting (increasing their molecular weight), said sulphurous saturated light compounds being sulphurous compounds whose boiling point is lower than the boiling point of thiophene, such as methanethiol, ethanethiol, and dimethyl sulphide. This makes it possible to produce a desulphurated gasoline fraction composed mainly of mono-olefins with 5 carbon atoms without loss of octane by simple distillation.

Under specific operating conditions, this hydrogenation selectively performs the hydrogenation of the diolefins present in the feed to be treated to mono-olefinic compounds, which have a better octane index. Another effect of selective hydrogenation is to prevent the progressive deactivation of the selective hydrodesulphuration catalyst and/or to avoid progressive plugging of the reactor due to the formation of polymerisation gums on the surface of the catalysts or in the reactor. Indeed, the polyunsaturated compounds are unstable and tend to form polymerisation gum precursors.

Patent application EP 2161076 discloses a process of selective hydrogenation of the polyunsaturated compounds, more particularly of the diolefins, allowing the weight increase of the sulphurous saturated light compounds to be performed conjointly. This process uses a catalyst containing at least one group VIb metal and at least one non-noble metal of group VIII deposited on a porous support. However, this document does not disclose catalysts allowing the performance of isomerisation of the external olefins into internal olefins. The present invention is distinct from the catalyst described in EP 2161076 notably in the selection of the following parameters taken in combination:

the specific surface area of the catalyst is within the range 200 to 270 $m^2/g$, the density of the group VIb element, expressed as the ratio of the content by weight of the oxide of the group VIb element to the specific surface area, is within the range 4 to $6.10^{-4}$ $g/m^2$;

the molar ratio of the group VIII metal to the group VIb metal is within the range 0.6 to 3 mol/mol.

The step of hydrodesulphuration of the cracking gasolines containing the mono-olefins consists of passing the feed to be treated, mixed with hydrogen, over a catalyst of the transition metal sulphide type in order to promote the reactions of reduction of the sulphur into hydrogen sulphide ($H_2S$). The reaction mixture is then cooled to condense the gasoline. The gaseous phase containing the excess of hydrogen and the $H_2S$ is separated, and the desulphured gasoline is recovered.

The residual sulphurous compounds generally present in the desulphured gasoline may be separated into two distinct families: the sulphurous, non-hydrogenated compounds present in the feed, and the sulphurous compounds formed in the reactor by secondary, "recombination" reactions. In the latter family of sulphurous compounds, those in the majority are the mercaptans arising from addition of the $H_2S$ formed in the reactor onto the mono-olefins present in the feed. The mercaptans of chemical formula R—SH, where R is an alkyl group, are also called recombination mercaptans, and generally represent between 20 wt. % and 80 wt. % of the residual sulphur in the desulphured gasolines.

Reduction of the content of recombination mercaptans can be achieved by catalytic hydrodesulphuration, but at the price of saturating a large part of the mono-olefins present in the gasoline, which then leads to a large reduction in the octane index of the gasoline, as well as an over-consumption of hydrogen. It is also known that the octane loss linked to hydrogenation of the mono-olefins during the hydrodesulphuration step increases in inverse proportion to the target sulphur content, that is to say, to when in-depth elimination of the sulphur compounds present in the feed is being attempted.

Moreover, Toba et al. (*Applied Catalysis B: Environmental* 70 (2007) 542-547) and Badawi et al. (*Journal of Molecular Catalysis A: Chemical* 320 (2010) 34-39) studied the influence of the structure of mono-olefinic compounds on their reactivity in the hydrodesulphuration (HDS) step, and demonstrated that mono-olefinic compounds having an internal double bond were more difficult to hydrogenate under the conditions of hydrodesulphuration.

To produce a gasoline having a low sulphur content and a good octane index, it appears advantageous to implement a first step of selective hydrogenation which achieves, conjointly, hydrogenation of the diolefins to olefins, weight increase of the sulphurous light compounds, and isomerisation of the external olefins to internal olefins so as to facilitate the functioning of the hydrodesulphuration process, as far as possible limit hydrogenation of the olefins and, as a consequence, limit the loss of octane index during the subsequent hydrodesulphuration step.

SUMMARY OF THE INVENTION

An aim of the present invention is to propose a process of improved selective hydrogenation of a gasoline containing polyunsaturated compounds and sulphurous light compounds which allows improved isomerisation of monounsaturated compounds having an external C═C double bond into an internal C═C double bond, while at the same time assuring the hydrogenation of the polyunsaturated compounds into monounsaturated compounds, and increasing weight of the sulphurous saturated light compounds by reacting with the unsaturated compounds.

The gasoline thus treated can be advantageously sent to a catalytic hydrodesulphuration unit the operating conditions of which enable the transformation of the organosulphurous compounds into H$_2$S while limiting hydrogenation of the olefins.

To this end, a process of selective hydrogenation is proposed which uses a catalyst containing at least one group VIb metal and at least one group VIII metal that are deposited on a porous support, wherein:
the content by weight of oxide of the group VIb element is within the range 6 to 18% with reference to the weight of the catalyst;
the content by weight of oxide of the group VIII element is within the range 4 to 12% with reference to the weight of the catalyst;
the specific surface area of the catalyst is within the range 200 to 270 m$^2$/g;
the density of the group VIb element, expressed as being the ratio between the said content by weight of oxide of the group VIb element and the specific surface area of the catalyst, is within the range 4 to 6.10$^{-4}$ g/m$^2$;
the molar ratio between the group VIII metal and the group VIb metal is within the range 0.6 to 3 mol/mol.

Surprisingly, the Applicants actually found that implementation of a process of hydrogenation in the presence of a catalyst as claimed enables the conjoint achievement of hydrogenation of the polyunsaturated compounds, and more particularly of the diolefins, increasing weight of the sulphurous light compounds, and more particularly of the mercaptans, as well as allowing the isomerisation of mono-olefinic compounds having an external C═C double bond into corresponding isomers with an internal C═C double bond.

The process according to the invention can be applied to any gasoline cut containing a certain proportion of diolefins and optionally also containing a number of lighter compounds belonging to cuts C3 et C4.

Another aim of the invention is to provide a gasoline desulphuration process yielding a product having a total S content of less than 50 ppm, and preferably less than 10 ppm, while limiting the loss of octane index.

To this end, a desulphuration process comprising the following steps is proposed:

a) a selective hydrogenation step implementing a process which uses a catalyst containing at least one group VIb metal and at least one group VII metal deposited on a porous support, wherein:
the content by weight of oxide of the group VIb element is within the range 6 to 18% with reference to the weight of the catalyst;
the content by weight of oxide of the group VIII element is within the range 4 to 12% with reference to the weight of the catalyst;
the specific surface area of the catalyst is within the range 200 to 270 m$^2$/g;
the density of the group VIb element, expressed as being the ratio between the said content by weight of oxide of the group VIb element and the specific surface area of the catalyst, is within the range 4 to 6.10$^{-4}$ g/m$^2$;
the molar ratio between the group VIII metal and the group VIb metal is within the range 0.6 to 3 mol/mol.

b) a step of separating the gasoline obtained in step a) into two factions comprising a light gasoline and a heavy gasoline respectively.

c) a treatment of the heavy gasoline separated in step b) on a catalyst enabling at least partial decomposition of the sulphur containing compounds into H$_2$S

DETAILED DESCRIPTION OF THE INVENTION

The invention relates to a process for treating gasolines comprising any type of chemical family, and notably diolefins, mono-olefins, and sulphurous compounds in the form of mercaptans and light sulphides. The present invention applies more particularly to the transformation of conversion gasolines, and in particular of the gasolines produced by catalytic cracking, fluidised-bed catalytic cracking (FCC), coking processes, visbreaking processes or pyrolytic processes. The feeds to which the invention applies have a boiling point within the range 0° C. to 280° C. The feeds may also contain hydrocarbons having 3 or 4 carbon atoms.

For example, the gasolines derived from catalytic cracking (FCC) units contain, on average, between 0.5 wt. % and 5 wt. % diolefins, between 20 wt. % and 50 wt. % mono-olefins, between 10 ppm and 0.5 wt. % sulphur, of which generally less than 300 ppm mercaptans. The mercaptans are generally concentrated in the light factions of gasoline, to be more precise, in the fraction the boiling temperature of which is below 120° C.

The gasoline treatment described in the present selective hydrogenation process consists principally of:
selectively hydrogenating the diolefins into mono-olefins;
transforming the sulphurous saturated light compounds, principally the mercaptans, into heavier sulphides or mercaptans by reaction with the mono-olefins;
isomerising the mono-olefinic compounds having an external C═C double bond into their isomer having an external C═C double bond.

The reactions of hydrogenation of the diolefins into mono-olefins are illustrated below by the transformation of 1,3-pentadiene, an unstable compound that is readily hydrogenated into pent-2-ene. However, it is sought to limit the secondary hydrogenation reactions of the mono-olefins which, in the example below, would lead to the formation of n-pentane.

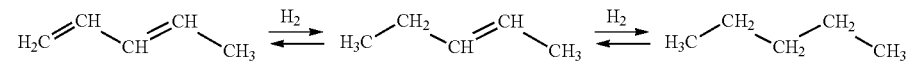

The sulphurous compounds to be transformed are principally the mercaptans and the sulphides. The principal reaction of mercaptan transformation consists in thioetherification of the mono-olefins by the mercaptans. The reaction is illustrated below by the addition of propane-2-thiol on to pent-2-ene to form a propyl pentyl sulphide.

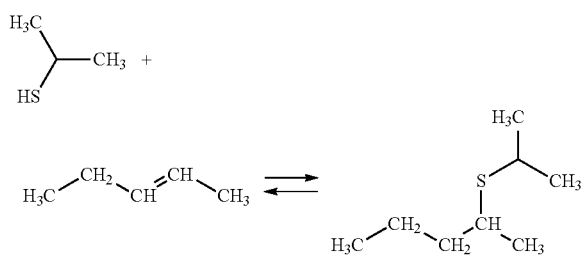

In the presence of hydrogen, the transformation of the sulphur compounds may also occur via the intermediary formation of $H_2S$, which may then combine with the saturated compounds present in the feeds by addition. However, this pathway is of minor importance under the preferred conditions of the reaction.

Other than the mercaptans, the compounds capable of being thus transformed and subjected to weight increase are the sulphides, principally dimethyl sulphide, methyl ethyl sulphide and diethyl sulphide, $CS_2$, COS, thiophane, and methylthiophane.

In some cases, weight increase reactions of the light nitrogenous compounds, principally nitriles, pyrrole and its derivatives, may also be observed.

According to the invention, the catalyst also enables isomerisation of the mono-olefinic compounds having their C=C double bond in an external position into their isomer with an internal C=C double bond.

This reaction is illustrated below by the isomerisation of hexene-1 to hexene-2 or hexene-3:

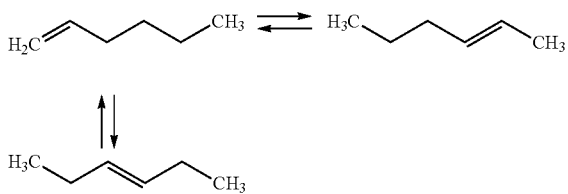

The process described in the present invention consists in placing the feed to be treated, in admixture with a hydrogen flow, with a catalyst containing at least one group VIb metal (group 6 according to the new notation of the periodic table of the elements: Handbook of Chemistry and Physics, 76th edition, 1995-1996) and at least one group VIII metal, (groups 8, 9 and 10) of the said classification, deposited on a porous, metal oxide-based support.

In particular, it has been found that the performances of the catalysts in isomerisation of external olefins into corresponding internal olefins are improved when the catalyst exhibits following features in combination:

The content by weight of the group VIb element in the form of the oxide is within the range 6 to 18 wt. %, preferably 8 to 12 wt. % and yet more preferably 10 et 12 wt. % with reference to the weight of the catalyst. The group VIb metal is preferably selected from molybdenum and tungsten. More preferably, the group VIb metal is molybdenum.

The catalyst also contains a group VIII metal preferably selected from nickel, cobalt and iron. More preferably, the group VIII metal is nickel. The content of group VIII metal expressed in the form of the oxide is within the range 4 to 12 wt. % and preferably 6 to 10 wt. % and yet more preferably 6 to 8 wt. % with reference to the weight of the catalyst.

The molar ratio of the non-noble group VIII metal to the group VIb metal is within the range 0.6 to 3 mol/mol, preferably 1 to 2 mol/mol.

The density of the group VIb element, expressed as the ratio of the said content by weight of oxide of the group VIb element to the specific surface area of the catalyst, is within the range 4 to $6.10^{-4}$ g/m$^2$, preferably 4.3 to $5.5.10^{-4}$ g/m$^2$, more preferably between 4.5 to $5.10^{-4}$ g/m$^2$. Thus, for example, in the situation in which the catalyst comprises 11 wt. % molybdenum oxide with reference to the weight of the catalyst and has a specific surface area of 219 m$^2$/g, the density of molybdenum, expressed as the ratio of the content by weight of molybdenum oxide to the specific surface area of the catalyst is equal to (0.11/219), or $5.10^{-4}$ g/m$^2$.

The specific surface area of the catalyst is within the range 200 to 270 m$^2$/g, preferably 220 to 260 m$^2$/g. The specific surface area is determined according to the ASTM standard D3663.

Preferably, a catalyst having a total pore volume greater than 0.3 cm$^3$/g measured by mercury porosimetry is used, preferably within the range 0.4 to 1.4 cm$^3$/g and preferentially within the range 0.5 to 1.3 cm$^3$/g. The mercury porosimetry is measured according to the ASTM standard D4284-92 using a wetting angle of 140°, with Micromeritics Autopore III equipment.

The catalyst support is preferably selected from alumina, nickel aluminate, silica, silicon carbide, or mixtures thereof. Alumina is preferably used and, yet more preferably, high-grade alumina.

According to one variant, the support consists of cubic gamma-alumina, or delta-alumina.

The catalyst according to the invention may be prepared by means of any methods known to the person skilled in the art, and notably by impregnation of the elements of groups VIII and VIb onto the selected support. This impregnation may, for example, be performed in accordance with the method known to the person skilled in the art by the terminology "dry impregnation", in which precisely the desired quantity of elements is introduced, in the form of soluble salts, into the selected solvent, for example, demineralised water, in order to fill the pores of the support as precisely as possible. The support being filled with the solution is preferably dried. The preferred support is alumina, which may be prepared starting with any type of precursor and moulding tools known to the person skilled in the art.

Following introduction of the elements of groups VIII and VIb, and optionally forming of the catalyst, the latter undergoes an activation treatment. The purpose of this treatment is generally to transform the molecular precursors of the elements into the oxide phase. In this case, the treatment is oxidising, but simple drying of the catalyst can also be performed. In the case of an oxidising treatment, also termed calcination, the catalyst is submitted to a heat treatment under air or under dilute oxygen, and the treatment temperature is generally within the range 200° C. to 550° C., preferably 300° C. to 500° C.

Salts of groups VIb and VIII metals that are usable in the process of preparation of the catalysts are, for example, cobalt nitrate, nickel nitrate, ammonium heptamolybdate, and ammonium metatungstate. Any other salt known to the person skilled in the art, that is of adequate solubility and decomposable during the activation treatment may also be used.

After calcination, the metals deposited on the support are in oxide form. In the case of nickel and molybdenum, the metals are principally in the form of $MoO_3$ and $NiO$. Prior to be contacted with the feed to be treated, the catalysts undergo a sulphuration step. The sulphuration is preferably performed in a sulphur-reducing environment, that is, in the presence of the $H_2S$ and of hydrogen, in order to transform the metal oxides into sulphides as such as e.g. $MoS_2$ and $Ni_3S_2$. The sulphuration is performed by injecting onto the catalyst a flux containing $H_2S$ and hydrogen, or a sulphurous compound capable to be degraded into $H_2S$ in the presence of the catalyst and of hydrogen. The polysulphides such as dimethyl disulphide are $H_2S$ precursors in current usage for catalyst sulphuration. The temperature is adjusted to react the $H_2S$ with the metal oxides to form metal sulphides. This sulphidation may be performed in situ or ex situ (inside or outside the reactor) of the hydrodesulphuration reactor at temperatures within the range 200 to 600° C. and more preferentially 300 to 500° C.

In order to be active, the metals must be substantially sulphured. An element is considered to be substantially sulphured when the molar ratio between the sulphur (S) present on the catalyst and the said element is at least equal to 60% of the theoretical molar ratio corresponding to the total sulphuration of the element under consideration:

$$(S/element)catalyst \geq 0.6 \times (S/element)theoretical$$

with:

(S/element)catalyst=molar ratio between the sulphur (S) and the element that are present on the catalyst (S/element)theoretical=molar ratio between the sulphur and the element corresponding to the total sulphuration of the element into the sulphide.

This theoretical molar ratio varies according to the element under consideration:
(S/Fe)theoretical=1
(S/Co)theoretical=8/9
(S/Ni)theoretical=2/3
(S/Mo)theoretical=2/1
(S/W)theoretical=2/1

When the catalyst comprises a plurality of metals, the molar ratio between the S present on the catalyst and all the elements together must similarly be at least equal to 60% of the theoretical molar ratio corresponding to the total sulphuration of each element into the sulphide, the calculation being performed pro rata with the molar fractions relating to each element.

For example, for a catalyst comprising molybdenum and nickel with a respective molar fraction of 0.7 et 0.3, the minimal molar ratio (S/Mo+Ni) is given by the equation:

$$(S/Mo+Ni)catalyst=0.6 \times \{(0.7 \times 2)+(0.3 \times (2/3))\}$$

The percentage sulphuration of the metals will very preferably be more than 80%.

The sulphuration is performed on the metals in the form of the oxide without a prior step of reduction of the metals being carried out. Indeed, the sulphuration of reduced metals is known to be more difficult than the sulphuration of metals in the form of oxides.

In the process of selective hydrogenation according to the invention, the feed to be treated is mixed with hydrogen before being put in contact with the catalyst. The quantity of hydrogen injected is such that the molar ratio between the hydrogen and the diolefins to be hydrogenated is greater than 1 (stoichiometry) and less than 10, and preferably within the range 1 to 5 mol/mol. Two large an excess of hydrogen can induce strong hydrogenation of the mono-olefins and, in consequence, a reduction in the octane index of the gasoline. The totality of the feed is generally injected at the inlet to the reactor. However, it may be advantageous in certain cases to inject a fraction or the totality of the feed between two consecutive catalytic beds placed in the reactor. This embodiment notably allows continued operation of the reactor if the inlet to the reactor becomes blocked by polymeric deposits, particles, or gums present in the feed.

The mixture composed of the gasoline and the hydrogen is put in contact with the catalyst at a temperature within the range 80° C. to 220° C., and preferably 90° C. to 200° C., with a liquid hourly space velocity (LHSV) within the range $1\ h^{-1}$ to $10\ h^{-1}$, the unit of liquid hourly space velocity being liter of feed per liter of catalyst per hour (l/l·h). The pressure is adjusted so that most of the reaction mixture is in liquid form in the reactor. The pressure is within the range 0.5 MPa to 5 MPa and preferably 1 to 4 MPa.

The gasoline treated under the conditions given above has a reduced diolefin and mercaptan content. The gasoline produced generally contains less than 1 wt. % diolefins, and preferably less than 0.5 wt. % diolefins. The sulphurous light compounds the boiling temperature of which is below that of thiophene (84° C.) are generally more than 50% converted. It is therefore possible to separate the light fraction of the gasoline by distillation and to send this fraction directly to the gasoline pool without complementary treatment. The light fraction of the gasoline generally has an endpoint below 120° C., and preferably below 100° C. and very preferably below 80° C.

The selective hydrogenation process according to the invention is particularly adapted to be implemented in the desulphuration process described in patent application EP 1 077 247.

The present application similarly has as its subject a process of desulphuration of gasoline comprising sulphurous compounds and consisting at least of the following steps:

a) a selective hydrogenation step implementing the process described above;

b) a step of separation of the gasoline obtained in step a) into two fractions comprising respectively a light gasoline and a heavy gasoline;

c) a step of treatment of the heavy gasoline separated in step b) on a catalyst allowing at least partial decomposition of the sulphurous compounds into $H_2S$.

Separation step b) is preferably performed by means of a conventional distillation column, also termed a splitter. This fractionation column must allow separation of a light gasoline fraction containing a small fraction of the sulphur, and a heavy fraction preferably containing the major part of the sulphur initially present in the initial gasoline.

This column generally operates at a pressure within the range 0.1 to 2 MPa and preferably 0.2 to 1 MPa. The number of theoretical plates of this separating column is generally within the range 10 to 100 and preferably 20 to 60. The rate of reflux, expressed as the ratio of the liquid flow in the column to the distillate flow expressed in kg/h, is generally less than unity and preferably less than 0.8.

The light gasoline obtained at the end of the separation generally contains at least the whole group of olefins in C5, preferably the compounds in C5 and at least 20% of the olefins in C6. This light fraction generally has a low sulphur content, that is to say it is not generally necessary to treat the light cut prior to using it as a fuel.

The desulphuration step c) is preferably a hydrodesulphuration step performed by passing the heavy gasoline, in the presence of hydrogen, over a catalyst comprising at least one group VIII element and/or at least one element from group VIb at least in part in sulphide form, at a temperature within the range of about 210° C. to about 350° C., preferably 220° C. to 320° C., under pressure generally within the range of about 1 to about 4 MPa, preferably 1.5 to 3 MPa. The hourly space velocity of the liquid is within the range about 1 to about 20 h$^{-1}$ (expressed as volume of liquid per volume of catalyst and per hour), preferably 1 to 10 h$^{-1}$, and very preferably 3 to 8 h$^{-1}$. The ratio H$_2$/feed is within the range 100 to 600 liters per liter and preferably 300 to 600 liters per liter.

The content of group VIII metal expressed as oxide is generally within the range 0.5 to 15 wt. %, preferentially 1 to 10 wt. % with reference to the weight of the catalyst. The content of group VIb metal expressed as oxide is generally within the range 1.5 to 60 wt. %, preferentially 3 to 50 wt. % with reference to the weight of the catalyst.

The group VIII element, when present, is preferably cobalt, and the group VIb element, when present, is generally molybdenum or tungsten. Combinations such as cobalt-molybdenum are preferred. The catalyst support is usually a porous solid such as, for example, an alumina, a silica-alumina or other porous solid as such as, for example, magnesium, silica or titanium oxide, alone or in admixture with alumina or silica-alumina. To minimise the hydrogenation of the olefins present in the heavy gasoline, it is advantageous to utilise preferentially a catalyst in which the density of molybdenum, expressed in wt. % of MoO$_3$ (the % by weight being expressed relative to the total weight of the catalyst) per unit of specific surface area is greater than 0.07 and preferably greater than 0.12. The catalyst according to the invention preferably has a specific surface area less than 250 m$^2$/g, more preferably less than 230 m$^2$/g, and very preferably less than 190 m$^2$/g.

The deposition of the metals on the support is achieved by all methods known to the person skilled in the art such as, for example, dry impregnation, by excess of a solution containing the metal precursors. The impregnation solution is selected so as to be able to solubilise the metal precursors in the desired concentrations. For example, in the case of synthesis of a CoMo catalyst, the molybdenum precursor may be the oxide of molybdenum, ammonium heptamolybdate and while the precursor of cobalt may for example be cobalt nitrate, cobalt hydroxide or cobalt carbonate. The precursors are generally dissolved in a medium allowing their solubilisation in the desired concentrations.

Following introduction of the element(s) and optionally forming of the catalyst, the catalyst is, in a first step, activated. This activation may correspond either to oxidation and then reduction, or to direct reduction, or to calcination alone. The calcination step is generally performed at temperatures between around 100 and around 600° C. and preferably within the range 200 to 450° C., under a flow of air. The reduction step is performed in conditions enabling conversion at least a part of the oxidised forms of the base metal into metal. Generally, said step consists in treating the catalyst under a flow of hydrogen at a temperature preferably at least equal to 300° C. The reduction may also be performed in part by means of chemical reducers.

The catalyst is preferably used at least in part in the sulphured form. The introduction of sulphur may occur before or after any activation step, that is calcination or reduction step. Preferably, no step of oxidation of the catalyst is performed when the sulphur or sulphurous compound has been introduced onto the catalyst. The sulphur or a sulphurous compound may be introduced ex situ, that is to say outside the reactor where the process according to the invention is carried out, or in situ, that is to say in the reactor used for the process according to the invention. In the latter case, the catalyst is preferably reduced under the conditions previously described, then sulphured by passage of a feed containing at least one sulphurous compound which, once degraded, leads to the fixation of the sulphur on the catalyst. This feed may be gaseous or liquid, for example hydrogen containing H$_2$S, or a liquid containing at least one sulphurous compound.

The sulphurous compound is preferably added onto the catalyst ex situ. For example, after the calcination step, a sulphurous compound may be introduced onto the catalyst in the presence optionally of another compound. The catalyst is subsequently dried, then transferred to the reactor serving for implementation of the process according to the invention. Within this reactor, the catalyst is then treated under hydrogen so as to transform at least a part of the principal metal into sulphide. The process which is especially advantageous for the invention is that described in the patents FR-B-2 708 596 and FR-B-2 708 597.

According to a particular embodiment of the invention, the desulphuration process further comprises a second step d) of treating the heavy gasoline treated in step c) on a catalyst enabling breakdown of the sulphurous compounds which would not have been broken down in H$_2$S in step c). The H$_2$S formed in step c) is advantageously eliminated before performing the treatment step d).

Example 1

The catalysts 1, 2, 3 and 4 were prepared by dry impregnation of a 100% alumina support.

The synthesis protocol consists in performing dry impregnation of an ammonium heptamolybdate and nickel nitrate solution, the volume of the aqueous solution containing the metallic precursors being equal to the volume of take-up in water corresponding to the mass of support to be impregnated (total volume of water capable of penetrating into the porosity). The concentrations of the precursors in the solution are adjusted so as to deposit on the support the desired contents by weight of metallic oxides.

The solid is then allowed to mature at ambient temperature for 12 hours, then dried at 120° C. for 12 hours. Finally, this solid is calcined at 500° C. for two hours under a flow of air (1 L/g·h).

The supports used are transition alumina of variable specific surface area, so as to obtain catalysts of various specific surface area following charging at equal content of metals. The characteristics of the catalysts thus prepared are given in Table 1.

TABLE 1

Characteristics of catalysts 1, 2, 3 and 4 in the form of the oxide.

| Catalyst | 1 (comparison) | 2 (comparison) | 3 (according to the invention) | 4 (according to the invention) |
|---|---|---|---|---|
| wt. % MoO$_3$ | 11 | 11 | 11 | 11 |
| wt. % NiO | 7 | 7 | 7 | 7 |
| Molar ratio Ni/Mo | 1.2 | 1.2 | 1.2 | 1.2 |
| dMoO$_3$ (10$^{-4}$ g/m$^2$ catalyst) | 8.9 | 5.8 | 4.8 | 4.3 |

TABLE 1-continued

Characteristics of catalysts 1, 2, 3 and 4 in the form of the oxide.

| Catalyst | 1 (comparison) | 2 (comparison) | 3 (according to the invention) | 4 (according to the invention) |
|---|---|---|---|---|
| Specific surface area of the catalyst ($m^2/g$) | 123 | 189 | 230 | 254 |

Catalysts 1 and 2 (not conforming to the invention) exhibit a specific surface area outside the range 200-270 $m^2/g$. Catalysts 3 and 4, on the other hand, have a specific surface area and a molybdenum density conforming to the invention.

The catalytic performances of the catalysts 1, 2, 3 and 4 were evaluated by means of a selective hydrogenation test conducted in a 500 ml agitated autoclave reactor. 4 g of catalyst are sulphured at atmospheric pressure on a sulphuration bench under a mixture of $H_2S/H_2$ consisting of 15 vol. % $H_2S$ at 1 L/g·h of catalyst and at 400° C. for two hours. This protocol enables sulphuration rates greater than 80% to be achieved for the group of catalysts conforming to the invention. The catalyst thus sulphured is transferred into the reactor under cover of air, then placed in contact with 250 mL of model feed at a total pressure of 1.5 MPa and a temperature of 160° C. The pressure is held constant during the test by a supply of hydrogen.

The feed used for the activity test is of the following composition: 1000 wt. ppm sulphur in methyl 3-thiophene form, 100 wt. ppm of sulphur in propane-2-thiol form, 10 wt. % olefin in the form of hexene-1, and 1 wt. % isoprene in n-heptane.

The time t=0 of the test corresponds to the placing in contact of the catalyst and the feed. The duration of the test is set to 80 minutes, and the gaseous-phase chromatographic analysis of the liquid effluent obtained enables evaluation of the activities of the different catalysts in hydrogenation of isoprene (formation of methylbutenes), hydrogenation of hexene-1 (formation of n-hexane), isomerisation of the hexene-1 (formation of hexene with saturation of internal positions, i.e. hexene-2 or hexene-3), and weight increase of light mercaptans (conversion of propane-2-thiol).

The activity of the catalyst for each reaction is defined relative to the rate constant obtained for each reaction normalised per gram of catalyst. The rate constant is calculated taking into consideration an order 1 for the reaction:

$A(X)=k(X)/m$ with:
A(X): activity of the catalyst for the reaction X, in $min^{-1}/g$ of catalyst
m: mass de catalyst (in the oxide form) engaged in the test
k velocity constant for the reaction under consideration, in $min^{-1}$ calculated according to the formula:

$k(X)=(1/80)*\ln(100/(100-Conv(X)))$ with 80: duration of the test in minutes
X=hexene corresponding to the isomerisation of the hexene
X=hexene corresponding to the hydrogenation of the hexene
X=isoprene corresponding to the hydrogenation of the isoprene The selectivity of the catalyst with regard to hydrogenation of the isoprene is equal to the ratio of the activities of the catalyst in hydrogenation of the isoprene and in hydrogenation of hexene-1: HYD (isoprene)/HYD (hexene-1)

The results obtained for the various catalysts are reported in Table 2 below on the basis of 100 with reference to catalyst 3 according to the invention.

TABLE 2

Performances of the catalysts in model molecule testing

| Catalyst | 1 (comparison) | 2 (comparison) | 3 (according to the invention) | 4 (according to the invention) |
|---|---|---|---|---|
| ISOM hexene rel/g | 58 | 78 | 100 | 109 |
| HYD hexene rel/g | 78 | 87 | 100 | 101 |
| HYD isoprene rel/g | 75 | 84 | 100 | 106 |
| HYD (isoprene)/A HYD (hexene-1) | 96 | 97 | 100 | 105 |

Catalysts 3 and 4 (implemented in the process according to the invention), the molybdenum density and specific surface area of which fall within the claimed ranges, show not only a hexene isomerisation activity which is distinctly greater than that of catalysts 1 and 2, but also an improved hydrogenation selectivity.

Example 2

The catalyst examples presented below allow an illustration of the influence of the density of group VIb metal (here molybdenum) of equal specific surface area of catalyst on the activity of hydrogenation of diolefins to mono-olefins, and of isomerisation of the "external" mono-olefins to "internal" mono-olefins.

Catalysts 5 and 6 (not conforming to the invention) were prepared according to the conditions in Example 1. These catalysts notably have a specific surface area of conforming to the invention, but a density of molybdenum outside the range $4\text{-}6.10^{-4}$ $g/m^2$. The characteristics of these two catalysts are grouped together in Table 3.

TABLE 3

Characteristics of catalysts 5 and 6 in the form of the oxide

| Catalyst | 5 (comparison) | 6 (comparison) |
|---|---|---|
| wt. % $MoO_3$ | 6 | 9 |
| wt. % NiO | 3.8 | 5.6 |
| Molar ratio Ni/Mo | 1.2 | 1.2 |
| $dMoO_3$ ($10^{-4}$ $g/m^2$ cata) | 2.4 | 3.8 |
| Specific surface area of catalyst ($m^2/g$) | 253 | 239 |

The catalytic performances of catalysts 5 and 6 are evaluated in the selective hydrogenation test described in Example 1 and compared with those of catalysts 3 and 4, which do conform to the invention.

TABLE 4

Performances of the catalysts in model molecule testing

| Catalyst | 5 (comparison) | 4 (according to the invention) | 6 (comparison) | 3 (according to the invention) |
|---|---|---|---|---|
| ISOM hexene rel/g | 69 | 109 | 82 | 100 |
| HYD hexene rel/g | 61 | 101 | 72 | 100 |
| HYD isoprene rel/g | 59 | 106 | 73 | 100 |
| HYD (isoprene)/HYD (hexene-1) | 97 | 105 | 101 | 100 |

By comparing catalysts 5 and 4 with catalysts 6 and 3, it is observed that, for equal specific surface area (around 250 and 230 m²/g respectively), a catalyst having a molybdenum density which falls within the claimed range possesses an activity of selective hydrogenation of diolefins and of isomerisation which are significantly more elevated than those of catalysts 5 and 6, the molybdenum density of which is located outside the range 4 to $6.10^{-4}$ g/m² ($2.4.10^{-4}$ g/m² and $3.8.10^{-4}$ g/m² respectively).

Example 3

Catalysts 7 (not conforming to the invention) and 8 (according to the invention) were prepared according to the conditions in Example 1. These catalysts are distinguished by their molar ratio of the group VIII metal to the group VIb metal.

TABLE 5

Characteristics of the catalysts 7 and 8 in oxide form

| Catalyst | 7 (comparison) | 8 (according to the invention) |
|---|---|---|
| wt. % MoO₃ | 11 | 11 |
| wt. % NiO | 3 | 11 |
| Molar ratio Ni/Mo | 0.5 | 1.9 |
| dMoO3 ($10^{-4}$ g/m² cata) | 4.5 | 5.0 |
| Specific surface area of the catalyst (m²/g) | 241 | 219 |

Catalysts 7 and 8 were evaluated using the selective hydrogenation test described in Example 1. The performances of the catalysts are grouped together in Table 6.

TABLE 6

Performances of the catalysts in model molecule testing

| Catalyst | 7 (comparison) | 8 (according to the invention) | 3 (according to the invention) |
|---|---|---|---|
| ISOM hexene rel/g | 71 | 112 | 100 |
| HYD hexene rel/g | 118 | 95 | 100 |
| HYD isoprene rel/g | 68 | 108 | 100 |
| HYD (isoprene)/A HYD (hexene-1) | 58 | 114 | 100 |

Catalyst 7 (not conforming), which has an Ni/Mo molar ratio outside the range 0.6-3 mol/mol but a molybdenum density and a specific surface area falling within the claimed ranges, exhibits a less good hydrogenation selectivity and a weaker isomerisation activity than catalysts 8 and 3 which have the Ni/Mo molar ratios of 1.9 and 1.2 respectively, the molybdenum densities respectively 5.0 and $4.8.10^{-4}$ g/m², conforming to the range 4 to $6.10^{-4}$ g/m², and the specific surface areas of respectively 219 and 230 m²/g, falling within the range 200-270 m²/g.

This example confirms that the technical effect sought is well obtained by implementing a catalyst which conforms to the group of parameters taken in combination and within the specific ranges claimed.

The invention claimed is:
1. A process of selective hydrogenation of a gasoline comprising polyunsaturated compounds and sulphurous light compounds, said process enables, conjointly, hydrogenation of the polyunsaturated compounds into monounsaturated compounds, weighting of the sulphurous saturated light compounds by reaction with the monounsaturated compounds, and isomerisation of the monounsaturated compounds comprising an external C=C double bond into their isomer having an internal C=C double bond, said process is conducted in the presence of a catalyst containing at least one group VIb metal and at least one group VIII metal deposited on a porous support, wherein:
   the content by weight of oxide of the group VIb element with reference to the weight of the catalyst is 6 to 18%;
   the content by weight of oxide of the group VIII element with reference to the weight of the catalyst is 4 to 12%;
   the specific surface area of the catalyst is 200 to 270 m²/g;
   the density of the group VIb element, expressed as being the ratio of the said content by weight of oxide of the group VIb element to the specific surface area of the catalyst, is $4\times10^{-4}$ g/m² to $6\times10^{-4}$; and
   the molar ratio between the group VIII metal and the group VIb metal is 0.6 to 3 mol/mol.
2. The process according to claim 1, wherein the group VIb metal is molybdenum or tungsten.
3. The process according to claim 1, wherein the group VIII metal is nickel, cobalt or iron.
4. The process according to claim 1, wherein the group VIII metal is nickel and the group VIb metal is molybdenum.
5. The process according to claim 1, wherein the content by weight of oxide of the group VIII element is 6 to 10%, with reference to the weight of the catalyst, and wherein the content by weight of oxide of the group VIb element is 8 to 12%, with reference to the weight of the catalyst.
6. The process according to claim 1, wherein the molar ratio of the group VIII metal to the group VIb metal is 1 to 2 mol/mol.
7. The process according to claim 1, wherein the density of the group VIb element is $4.3\times10^{-4}$ g/m² to $5.5\times10^{-4}$ g/m².
8. The process according to claim 1, wherein the sulphuration rate of the group VIb metal and the group VIII metal of the catalyst is greater than 80%.
9. The process according to claim 1, wherein the catalyst has a total pore volume greater than 0.3 cm³/g.
10. The process according to claim 1, wherein the specific surface area of the catalyst is 220 to 260 m²/g.

11. The process according to claim 1, wherein the support is alumina, silica, silicon carbide or a mixture thereof.

12. The process of selective hydrogenation according to claim 1, wherein the feed and the hydrogen are put in contact with the catalyst at a temperature of 80° C. to 220° C. and with a liquid hourly space velocity of 1 h$^{-1}$ and 10 h$^{-1}$ and a pressure of 0.5 to 5 MPa.

13. A process of desulphuration of gasoline comprising sulphurous compounds, comprising the following steps:
   a) a selective hydrogenation step, which is the selective hydrogenation of a gasoline comprising polyunsaturated compounds and sulphurous light compounds to produce a hydrogenated gasoline, said selective hydrogenation step enables, conjointly, hydrogenation of the polyunsaturated compounds into monounsaturated compounds, weighting of the sulphurous saturated light compounds by reaction with the monounsaturated compounds, and isomerisation of the monounsaturated compounds comprising an external C═C double bond into their isomer having an internal C═C double bond, said selective hydrogenation step is conducted in the presence of a catalyst containing at least one group VIb metal and at least one group VIII metal deposited on a porous support, wherein:
      the content by weight of oxide of the group VIb element with reference to the weight of the catalyst is 6 to 18%;
      the content by weight of oxide of the group VIII element with reference to the weight of the catalyst is 4 to 12%;
      the specific surface area of the catalyst is 200 to 270 m$^2$/g;
      the density of the group VIb element, expressed as being the ratio of the said content by weight of oxide of the group VIb element to the specific surface area of the catalyst, is $4\times10^{-4}$ g/m$^2$ to $6\times10^{-4}$ g/m$^2$; and
      the molar ratio between the group VIII metal and the group VIb metal is 0.6 to 3 mol/mol;
   b) a step of separating the hydrogenated gasoline obtained in step a) into two fractious comprising a light gasoline and a heavy gasoline; and
   c) a treatment step of the heavy gasoline separated in step b) on a catalyst allowing sulphurous compounds present in said heavy gasoline to be at least partially broken down to H$_2$S.

14. The process according to claim 13, wherein the treatment step c) is performed in the presence of hydrogen, and a catalyst comprising at least one group VIII element and/or at least one group VIb element at least in part in sulphide form, at a temperature of 210° C. to 350° C., at a pressure of 1 to 4 MPa, and with a space velocity expressed as the volume of liquid per volume of catalyst and per hour of 1 h$^{-1}$ and 20 h$^{-1}$.

15. The process according to claim 13, wherein the catalyst of step c) comprises a content of group VIII metal expressed in the form of the oxide of 0.5 to 15 wt. %, with reference to the weight of the catalyst, and a content of group VIb metal expressed in the form of the oxide of 1.5 to 60 wt. %, with reference to the weight of the catalyst.

16. The process according to claim 13, wherein the catalyst of step c) comprises a content of group VIII metal expressed in the form of the oxide of 1 to 10 wt. %, with reference to the weight of the catalyst, and a content of group VIb metal expressed in the form of the oxide of 3 to 50 wt. %, with reference to the weight of the catalyst.

17. The process according to claim 1, wherein the group VIb metal is molybdenum.

18. The process according to claim 1, wherein the group VIII metal is nickel.

19. The process according to claim 1, wherein the content by weight of oxide of the group VIII element is 6 to 8%, with reference to the weight of the catalyst, and wherein the content by weight of oxide of the group VIb element is 10 to 12%, with reference to the weight of the catalyst.

20. The process according to claim 1, wherein the density of the group VIb element is $4.5\times10^{-4}$ g/m$^2$ to $5\times10^{-4}$ g/m$^2$.

\* \* \* \* \*